United States Patent [19]

Kobayashi et al.

[11] 4,096,050
[45] Jun. 20, 1978

[54] OXYGEN DETECTOR

[75] Inventors: Nobuyuki Kobayashi, Toyota; Mitsuo Kawai, Okazaki, both of Japan

[73] Assignee: Toyota Jidosha Kogyo Kabushiki Kaisha, Toyota, Japan

[21] Appl. No.: 750,879

[22] Filed: Dec. 15, 1976

[30] Foreign Application Priority Data

Sep. 21, 1976 Japan ............................. 51-126998[U]

[51] Int. Cl.² ........................................... G01N 27/46
[52] U.S. Cl. ............................. 204/195 S; 123/119 E
[58] Field of Search ......................... 204/1 S, 195 S; 123/119 E

[56] References Cited

U.S. PATENT DOCUMENTS 3,546,086  12/1970  Sayles ........................... 204/195 S
3,835,012  9/1974  Hemak ........................... 204/195 S
3,844,920  10/1974  Burgett et al. .................. 204/195 S

FOREIGN PATENT DOCUMENTS 2,416,629  10/1975  Germany ........................ 204/195 S Primary Examiner—T. Tung
Attorney, Agent, or Firm—Stevens, Davis, Miller & Mosher

[57] ABSTRACT

An oxygen detector of the type having a tubular ceramic or zirconia electrode covered with a very thin platinum layer and a cylindrical protective cover for the electrode, the cover having a plurality of small openings arranged in its cylindrical wall to be substantially more dense on one side thereof than on the diametrically opposite side thereof, the detector being adapted to be positively mounted to make the aforementioned opposite side face upstream of the gas stream in which the detector is positioned.

3 Claims, 2 Drawing Figures

OXYGEN DETECTOR

BACKGROUND OF THE INVENTION

1. Field of the Invention

The present invention relates to an oxygen detector adapted to be mounted in exhaust manifolds or pipes forming the exhaust system of an automobile for detecting the residual oxygen content in the exhaust gasses.

2. Description of the Prior Art

Oxygen detectors for the aforementioned purpose are of course known. The detector generally comprises a body enclosing a solid electrolyte oxygen sensor at one end thereof, said sensor generally including a tubular element closed at one end thereof, said tubular element being made of a ceramic or zirconia and covered with very thin platinum layers at its inner and outer surfaces. A flange is usually connected to the body for mounting it at a wall portion of an exhaust manifold or pipe of an engine in a manner such that the sensor end of said body is inserted into the exhaust manifold or pipe through an opening formed in the wall portion of the exhaust manifold or pipe. Furthermore, a cylindrical protective cover is mounted over said sensor for protecting the aforementioned very delicate structure of the solid electrolyte oxygen sensor. The conventional protective cover is generally formed with a plurality of small openings arranged uniformly in its entire cylindrical wall so that the detector may be mounted to the wall portion of an exhaust manifold or pipe in any direction or angle around the central axis of the detector body.

In view of effecting a quick responsive feedback control for the intake system of an engine, it is desirable that the oxygen detector be located as close to the exhaust port of the engine as possible in the exhaust system. Furthermore, since the solid electrolyte oxygen sensor of the aforementioned platinum type can operate in a normal condition when the electrode is heated at or above a predetermined relatively high temperature (generally 400° C.), it is also desirable from this point of view that the oxygen detector be located closer to the exhaust port so that the sensor is heated up to the high temperature by exhaust gasses of a higher temperature within a short period after the starting up of the engine. If the oxygen detector is located very close to the exhaust port, it is naturally exposed to a strong hot stream of exhaust gasses. In this case, if the protective cover mounted over the solid electrolyte oxygen sensor is formed with a lot of small openings arranged uniformly in its entire cylindrical wall as in the conventional detectors, a strong gas flow impingement on the sensor surface will occur in the up-stream side thereof thereby generating hot spots in the platinum layer where it will bulge out and finally there is a danger that the very thin platinum layer is exfoliated.

SUMMARY OF THE INVENTION

It is therefore the object of the present invention to provide an oxygen detector which can be used safely even when it is exposed to a strong hot stream of exhaust gasses located very close to the exhaust port of an internal combustion engine.

According to the present invention, the above mentioned object is accomplished by an oxygen detector comprising a body including a solid electrolyte oxygen sensor at one end thereof, a flange connected to said body for mounting said body at a wall portion of an exhaust manifold or pipe of an engine in a manner such that said sensor end of said body is inserted into said exhaust mainfold or pipe through an opening formed in said wall portion of the exhaust manifold or pipe, and a cylindrical protective cover mounted over said sensor, said cover having a plurality of small openings in its cylindrical wall, said openings being arranged to be substantially more dense on one side thereof than on the diametically opposite side thereof, said flange having mounting holes arranged asymmetrically with each other with respect to a central axis of said body. In this case, the side of the cylindrical cover where the small openings are provided in a higher density is, of course, positioned at the downstream side of the gas stream and this positioning of the oxygen detector is ensured by the provision that the flange has the mounting holes arranged asymmetrically with each other with respect to a central axis of the body and, consequently, the mounting direction of the oxygen detector is positively determined. By this arrangement the hot gasses of the strong hot gas stream contact the solid electrolyte oxygen sensor principally after they have turned around through the openings provided at the downstream side of the cylindrical cover as slow speed streams in a well diffused manner, whereby any hot spot generation is avoided in the platinum sensor surface. The wall portion of the cylindrical cover which is located at the front side of the cover and faces the stream of exhaust gasses may be free of any openings or may be formed with a very few openings. The asymmetrical arrangement of the mounting holes with respect to the central axis of the body may be accomplished in various manners such as to deflect two opposite holes angularly from diametrical alignment or to vary the radial distance of individual mounting holes.

BRIEF DESCRIPTION OF THE DRAWING

In the accompanying drawing.

DESCRIPTION OF THE PREFERRED EMBODIMENT

Figure 1:
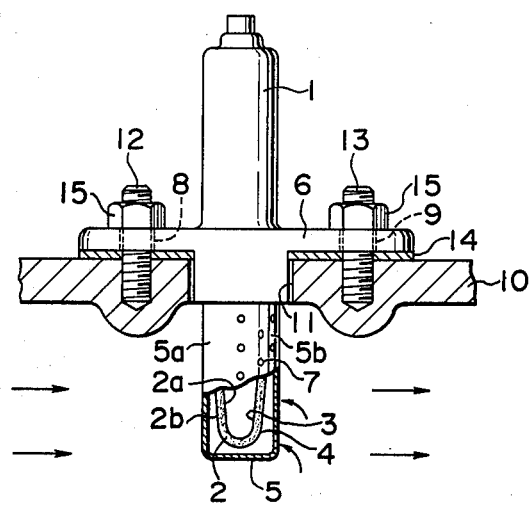
FIG. 1 is a side view partly in section of an embodiment of the oxygen detector of the present invention as mounted in a wall portion of an exhaust manifold or pipe of an engine.
Figure 2:
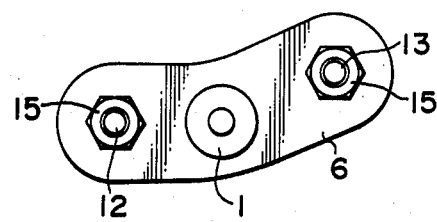
FIG. 2 is a plan view of the detector shown in FIG. 1.

In the following the invention will be explained in more detail with reference to the accompanying drawing.

As shown in the drawing, the oxygen detector comprises a body 1 including a solid electrolyte oxygen sensor 2 at one end thereof, said sensor being formed in a tubular shape closed at one end and being made of ceramic or zirconia. The inside surface 2a and the outside surface 2b of the tubular element are covered with very thin layers of platinum 3 and 4, respectively. The sensor 2 is covered by a cylindrical protection cover 5 which is mounted to the body 1 at one end thereof and is closed by an end wall at its opposite free end. A mounting flange 6 is connected to the body 1. The flange 6 may conveniently be formed as an integral part of the body 1 so as to provide an integral housing for the oxygen detector. In the shown embodiment, a diametrical half portion of the cylindrical cover 5, i.e. the half portion 5a, is completely closed with no opening formed therein, whereas the opposite half portion 5b is formed with a number of small openings 7.

In the shown embodiment, the flange 6 has two mounting holes 8 and 9 for passing mounting bolts 12 and 13 therethrough. As apparent from the figure, the holes 8 and 9 are arranged asymmetrically with each other with respect to a central axis of the body 1 by being deflected angularly from the diametrical alignment with each other and by being located at different radial distances from the central axis as well. Of course, the angular deflection and the difference in the radial distance need not be simultaneously effected and either of the two is enough to ensure a positive determination of the mounting direction of the oxygen detector. The numeral 10 designates a wall portion of an exhaust manifold or pipe of an engine located close to the exhaust port. An opening 11 is formed in the wall portion and two stud bolts 12 and 13 are mounted to the wall portion at proper relative positions with respect to the opening 11 corresponding to the relative position of the mounting holes 8 and 9 with respect to the body 1.

In mounting, the stud bolts 12 and 13 are mounted beforehand to the wall portion 10 and a proper gasket means 14 is placed on the wall portion around the opening 11. Then the oxygen detector is mounted to the wall portion in a manner such that the covered end thereof is inserted into the opening 11 while the holes 8 and 9 of the flange 6 engage with the stud bolts 12 and 13. The simultaneous engagement between the covered end of the body and the opening 11 and two stud bolts 12 and 13 and two holes 8 and 9 is possible only when the oxygen detector is mounted to the wall portion in a correct design direction. Thereafter, nuts 15 are mounted onto the stud bolts and fastened. Thus, the correct mounting of the oxygen detector is automatically accomplished, wherein the portion 5a faces the upstream of the exhaust gas stream flowing in the exhaust manifold or pipe while the portion 5b with small openings 7 faces the downstream side of the gas stream.

In operation, a strong hot stream of exhaust gasses impinges only on the portion 5a which does not allow the strong hot stream to directly impinge on the very thin platinum layered sensor surface. The gas stream flowing over the side and rear portion 5b having small openings 7 formed therein turns into the openings at a relatively low speed so that the gas stream which has entered into the interal space of the cover 5 through the openings 7 immediately diverges before it contacts the sensor surface. Thus, the entire outer surface of the sensor is uniformly swept by a soft flow of exhaust gasses which is continously refreshed by the supply of new gasses constantly flowing into the internal space of the cover through a lot of small openings 7. When the sensor is heated up to a determined high temperature such as about 400° C, the platinum layer operates as a catalyst and the combustible components and residual oxygen contained in the exhaust gasses rapidly react on the surface of the platinum layer and the existance of the residual oxygen is detected in accordance with the principle of operation which per-se is well known in the art.

From the foregoing, it will be appreciated that the oxygen detector of the present invention can be located very close to the exhaust port of the engine despite its exposure to a strong hot stream of exhaust gasses so that its sensor is warmed up in a very short period after the starting up of the engine and a quick responsive feedback control of the intake system is effected by checking the exhaust gasses immediately at the exit of the exhaust port.

Although the invention has been described with respect to a particular embodiment thereof, it will be understood by those skilled in the art that various modifications can be made with respect to the shown embodiment without departing from the spirit of the invention.

We claim:
1. An oxygen detector comprising:
   a body including an elongated solid electrolyte oxygen sensor at one end thereof;
   a flange connected to said body substantially at right angles to the central axis of said sensor for mounting said body to a wall portion of an exhaust manifold or pipe of an engine in a manner such that said sensor end of said body is inserted into said exhaust manifold or pipe through an opening formed in said wall portion of said exhaust manifold or pipe, said flange having mounting holes arranged asymmetrically with each other with respect to the central axis of said body, and,
   a cylindrical protective cover having a first closed free end and a second end mounted to said body in a manner of enclosing said sensor therein, said cover having a large number of small openings bored in its cylindrical wall, said openings being arranged substantially on one diametrical half side of said cylindrical wall.

2. The oxygen detector of claim 1, wherein the asymmetrical arrangement of the mounting holes is effected by deflecting the holes angularly from diametrical alignment.

3. The oxygen detector of claim 1, wherein the asymmetrical arrangement of said mounting holes is effected by varying the radial distance of the individual holes from the central axis of said body.

* * * * *